US010772927B2

(12) United States Patent
Adell Winkler et al.

(10) Patent No.: US 10,772,927 B2
(45) Date of Patent: Sep. 15, 2020

(54) USE OF A CASEIN HYDROLYSATE AS AN ANTIVIRAL AGENT

(71) Applicant: NTD LABS, S. L., Terrassa (ES)

(72) Inventors: Pere Adell Winkler, Terrassa (ES); Guillermo Lopez Zarco, Terrassa (ES)

(73) Assignee: NTD Labs, S.L., Terrassa (ES)

(*) Notice: Subject to any disclaimer, the term of this patent is extended or adjusted under 35 U.S.C. 154(b) by 0 days.

(21) Appl. No.: 15/121,080

(22) PCT Filed: Feb. 17, 2015

(86) PCT No.: PCT/IB2015/051157
§ 371 (c)(1),
(2) Date: Aug. 24, 2016

(87) PCT Pub. No.: WO2015/125067
PCT Pub. Date: Aug. 27, 2015

(65) Prior Publication Data
US 2016/0361374 A1 Dec. 15, 2016

(30) Foreign Application Priority Data
Feb. 24, 2014 (ES) .................................. 201430248

(51) Int. Cl.
A61K 38/01 (2006.01)
A61K 9/00 (2006.01)
A61K 9/14 (2006.01)
A61K 35/20 (2006.01)

(52) U.S. Cl.
CPC ............ A61K 38/018 (2013.01); A61K 9/009 (2013.01); A61K 9/0014 (2013.01); A61K 9/0053 (2013.01); A61K 9/14 (2013.01); A61K 35/20 (2013.01); A61K 38/01 (2013.01); Y02A 50/467 (2018.01)

(58) Field of Classification Search
CPC .. A61K 38/018; A61K 9/0014; A61K 9/0053; A61K 9/009; A61K 35/20; A61K 38/017; A61K 9/14
See application file for complete search history.

(56) References Cited

U.S. PATENT DOCUMENTS 6,670,118 B2* 12/2003 Hirschman .......... A61K 47/645
                                                        435/6.16
2005/0148504 A1* 7/2005 Katunuma ......... A61K 38/1709
                                                        424/94.63
2010/0112635 A1* 5/2010 Edens ...................... A23J 3/16
                                                        435/68.1
2010/0317601 A1* 12/2010 Sidelman .......... A61K 38/1709
                                                        514/21.3

FOREIGN PATENT DOCUMENTS

| DE | 3922453 A1 | 1/1991 |
|---|---|---|
| WO | 92/17191 A1 | 10/1992 |
| WO | 00/01720 A2 | 1/2000 |
| WO | 02/45524 A2 | 6/2002 |
| WO | 2004047566 A1 | 6/2004 |
| WO | 2011138489 A1 | 11/2011 |
| WO | 2014/008248 A2 | 1/2014 |
| WO | 2014/030125 A2 | 2/2014 |

OTHER PUBLICATIONS

Sarah A Dabydeen, The role of NH4CI and cysteine proteases in Human Papillomavirus type 16 infection, Virology Journal 2009, 6:109.*
Ian M. Mackay, An Opportunistic Pathogen Afforded Ample Opportunities: Middle East Respiratory Syndrome Coronavirus, Viruses, 2017.*
Amar Safdar, Infections in Patients With Hematologic Neoplasms and Hematopoietic Stem Cell Transplantation: Neutropenia, Humoral, and Splenic Defects, Clinical Infectious Diseases 2011;53(8):798-806.*
https://www.emedicinehealth.com/genital_warts/article_em.htm#facts_and_definition_of_genital_warts_hpv_infection, Published on line May 2006.*
International Search Report dated Jun. 1, 2015 in corresponding Application No. PCT/IB2015/051157; 4 pgs.
Rodriguez Saint-Jean S et al., Antiviral activity of casein and αs2 casein hydrolysates against the infectious haematopoietic necrosis virus, a rhabdovirus from salmonid fish, Journal of Fish Diseases, May 2013, vol. 36, No. 5, pp. 467-481.

* cited by examiner

Primary Examiner — Rachael E Bredefeld
Assistant Examiner — Erinne R Dabkowski
(74) Attorney, Agent, or Firm — Servilla Whitney LLC

(57) ABSTRACT

The present invention relates to the use of a casein hydrolysate as an antiviral agent for the treatment of opportunistic virus infections, especially herpesvirus and human papillomavirus. This casein hydrolysate has an application in both the therapeutic treatment of established symptoms and the prevention of the infection or the reactivation of a latent infection by an opportunistic virus. The casein hydrolysate of the present invention is effective for the prevention of opportunistic virus infections in individuals with weakened immune system.

19 Claims, No Drawings

USE OF A CASEIN HYDROLYSATE AS AN ANTIVIRAL AGENT

TECHNICAL FIELD

The present invention relates to products for the treatment and prevention of viral diseases caused by opportunistic virus.

TECHNICAL BACKGROUND

Among the viruses responsible for the many and diverse viral diseases, a type of viruses known as opportunistic viruses can be distinguished, that are characterized because, although they may affect the general population, the occurrence of their infections is particularly high in individuals with impaired immune system, for example, in patients infected with the human immunodeficiency virus (HIV) or in transplanted patients, in which their pathological effects are manifested in a particularly virulent way.

Among the viruses usually included within the group of opportunistic viruses are mainly herpesvirus and human papillomavirus, as well as Molluscum contagiosum virus, hepatitis B virus, hepatitis C virus, JC virus, and BK virus, as described, for example, in the publications Salavert et al. *Role of viral infections in immunosuppressed patients*, Med. Intensiva, 2011, 35 (2), pp 117-125; and U. Banarjee, *Progress in diagnosis of opportunistic infections in HIV/AIDS*, Indian J. Med. Res., 2005, 121, pp 395-406.

Herpesviruses belong to the Herpesviridae family, and are DNA viruses. They are composed of a DNA strand surrounded by an icosahedral capsid; it, in turn, is surrounded by a tegument and a membrane arranged as an envelope.

Eight different species have been identified among the herpesviruses: herpes simplex virus type 1 (HSV-1), type 2 (HSV-2), varicella zoster virus (VZV), Epstein-Barr virus (EBV), cytomegalovirus (HCMV) and herpesvirus type 6 (HHV-6), 7 (HHV-7) and 8 or Kaposi's Sarcoma herpesvirus (HHV-8, KSHV).

All of them share the common feature that, after infection, they may remain in a latent state, alternating latent periods with reactivation periods throughout the whole life of the infected individual. The latency period is characterized by a minimal expression of the viral gene and the absence of synthesis of new viruses.

Usually a distinction can be drawn between primary infection, referred to the first infection of the subject by the virus, which usually occurs in childhood or adolescence and which is often asymptomatic, and the subsequent reactivations which lead to recurrent injuries.

Diseases caused by herpesvirus infection are diverse due to the variety of the viruses and also because most of them can interact with the infected patient in more than one way and cause more than one pathology.

Thus, for example, the VZV virus is the responsible for varicella as a primary infection, whereas the reactivation of the latent virus in adults leads to herpes zoster. Herpes zoster affects the peripheral nerves and the skin, and can show serious complications, especially in individuals with alterations in their immune system.

EBV virus is the cause of infectious mononucleosis, particularly in adolescents. The EBV latent infection can be reactivated, especially in HIV-positive patients, resulting in the hairy leukoplakia. Also, the infection by said virus can lead to malignant lesions such as nasopharyngeal carcinoma, Burkitt's lymphoma, B cell lymphoma or oral carcinoma.

Cytomegalovirus infection can lead to the perinatal disease, acute HCMV infection, and to the worsening of opportunistic infections in immunocompromised subjects, for example, in transplanted or HIV infected patients.

The most frequent herpesviruses are herpes simplex HSV-1 and HSV-2, which are responsible for a large variety of infections involving vesicular eruptions on the skin and mucous membranes, and that can also occasionally affect the central nervous system and visceral organs.

HSV-1 infection is mainly associated with the orofacial region, causing infections from mild, such as herpes labialis, to severe, such as viral encephalitis. The most common injury associated with HSV-1 is herpes labialis, although it can also cause other pathologies such as, for example, primary herpetic gingivostomatitis, recurrent intraoral herpes and ocular herpes simplex.

HSV-2 causes injuries that are similar to oral herpes, but which occur mainly in the genital region (genital herpes), although it may also be involved in herpes labialis. The genital herpes has been associated with an increased risk of HIV transmission, and vice versa, due to the presence of genital ulcers.

Exceptionally, the reactivation or primary infection with herpes simplex virus can cause other serious and high mortality diseases, such as pneumonitis, hepatitis, tracheobronchitis or disseminated infection.

For its part, human papillomavirus (HPV) belongs to the family of Papillomaviridae, and are also DNA viruses which have a double-stranded DNA and are characterized for being non-enveloped.

To date, more than 100 different types of HPVs have been identified, which can be divided into cutaneous or mucosal, depending on the tissues susceptible to be infected, so that cutaneous HPVs infect and replicate in the squamous epithelium of the skin, causing warts, while mucosal HPVs infect and replicate in the mucosal membranes, resulting in genital, oral and conjunctival papillomas, as described for example in Woon-Won et al., *Strategies against Human Papillomavirus infection and cervical cancer*, J. Microbiol., 2004, 42 (4), pp 255-266.

HPV infection is often asymptomatic, so that it is estimated that in many individuals infected with this virus the infection is in a latent state.

HPV infection can cause a wide variety of clinical conditions, ranging from minor injuries to some types of cancers, especially cancer of the cervix (or cervical cancer), vaginal, anal, vulvar, penile or oropharyngeal cancers.

Benign infections associated with HPV are usually reduced to warts, of the plantar, common, flat or genital (condyloma) types.

HPV is considered the most common sexually transmitted viral disease worldwide, so about 30 sexually transmitted types have been identified, that primarily infect the neck of the womb (or cervix), vagina, vulva, penis and anus. They are often classified ranging from "low risk", associated with genital warts, to "high risk", associated with intraepithelial cervical lesions and cancers of the lower genital tract. Among the high-risk HPVs, four types stand out, that are those more often found in malignant cervical cancer cells, which are called type 16, 18, 31 and 45. It is believed that HPV is involved in practically all cases of cervical cancer.

Frequently, prior to the development of cervical cancer, premalignant or precancerous lesions appear, such as cervical dysplasia of the cervical cells, which can subside spontaneously, but involve some risk of becoming cancerous lesions.

Among the conditions of the mucous membranes, recurrent respiratory papillomatosis and focal epithelial hyperplasia (Heck's disease) may also be highlighted, as well as papillomas or carcinomas of the conjunctiva.

The greater or lesser severity of the pathologies derived from HPV infection is largely related to the immune level of infected patients, so an increased risk of developing HPV-derived neoplasms has been detected in HIV-infected patients or in transplanted patients.

Another opportunistic virus is the so called Molluscum contagiosum (MCV), a DNA virus belonging to the family of Poxviridae, whose infection causes the skin disease known as molluscum contagiosum, which causes papules or nodules.

The virus spreads by direct contact with lesions or through contaminated objects and also spreads by sexual contact. In patients with normal immune systems, the lesions usually disappear spontaneously after a certain period of time, but in immunocompromised individuals, the infection usually shows more severe and persistent clinical symptoms.

For its part, the JC virus or John Cunningham virus (JCV) is a DNA virus of the family of Polyomaviridae. Typically, the infection with this virus is asymptomatic and the virus remains latent in infected individuals.

However, when there are alterations in the immune system, typically in transplanted or HIV-positive patients, the JC virus can reactivate and lead to progressive multifocal leukoencephalopathy, a serious disorder that is characterized by the loss of myelin that covers and protects the nerves in the brain.

The BK virus is another opportunistic virus from the same family, which has a remarkable genetic similarity with the JC virus. Like that one, the infection in most of the infected population is mild or asymptomatic, but it can reactivate in immunocompromised patients, particularly in kidney transplant patients, in which it can lead to certain diseases such as hematuria, hemorrhagic cystitis, urethral stenosis and interstitial nephritis.

Finally, within the group of opportunistic viruses, it is worth mentioning hepatitis B virus (HBV), from the family of Hepadnaviridae, and hepatitis C virus (HCV), from the family of Flaviviridae.

Infection with hepatitis B virus can cause mild discomfort or be asymptomatic. It can also cause a chronic inflammation of the liver, and in that case it is known as a chronic hepatitis B, which can occasionally progress to cirrhosis and may increase the probability of contracting hepatocellular carcinoma. Hepatitis B spreads through contact with blood, semen or other fluids from an infected person.

Similarly, infection with hepatitis C virus can show mild symptoms or be asymptomatic, but chronic infection can lead to scarring of the liver, cirrhosis, and occasionally lead to liver cancer. The virus usually spreads through contact with infected blood.

Generally, there are no specific treatments entirely satisfactory for the disorders caused by these viruses, hence therapy is based on the use of certain antiviral products, and in some cases in vaccination, depending on the type of infection.

Thus, for example, the most widely used therapy for treating herpesvirus infections is aciclovir, especially for genital herpes, herpes labialis or herpes zoster, and it may be administered topically, orally or intravenously, depending on the type and severity of the pathology. Other antivirals that are also used as antiherpetics are, for example, valaciclovir, famciclovir, penciclovir, ganciclovir, foscarnet, and cidofovir, among others.

These drugs are not actually a cure that completely eliminates the herpesvirus infection from the organism, but rather they are used to mitigate the infection outbreaks, to help to reduce the pain and to make the symptoms disappear faster.

As for the human papillomavirus (HPV), currently there is no specific treatment for the infections caused by this virus. The main therapeutic strategies are based on the general stimulation of the cellular immune system, avoiding the replication, transcription and transformation of the virus, and the use of prophylactic vaccines and curative vaccines.

In the case of warts caused by this virus, as well as molluscum contagiosum, the treatment is based mainly on local removal methods, for example based on surgery, electrocautery, cryosurgery or laser therapy, which however can lead to the appearance of scarring and recurrence. Destructive chemical methods are also used, for example with trichloroacetic or bichloracetic acid, though such treatments cause irritation and are not uniformly effective. Antiviral products such as cidofovir or immunomodulators as imiquimod are also used topically, but they can also cause skin irritation.

For the treatment of cervical lesions associated with HPV, different antiviral and immunomodulatory agents have been used, particularly cidofovir, podophyllin, and also interferons. In recent years, efforts have focused primarily on the development of prophylactic vaccines for the prevention cervical cancer, as described in the article Gersch et al., *New approaches to prophylactic human papillomavirus vaccines for cervical cancer prevention*. Antivir. Ther., 2012, 17(3), pp 1-13. There is also a vaccine against hepatitis B virus (HBV).

None of the drugs available for the treatment of these viral infections has proved to be completely effective. Moreover, all of them have certain side effects. For example, antiviral drugs such as acyclovir, administered locally can cause irritation and burning, while administered orally, can occasionally lead to gastrointestinal disturbances, headache, and less frequently, renal insufficiency or neurotoxicity.

Moreover, continued use of antiviral drugs may cause resistance and lack of effectiveness in the long term. In this regard, different approaches have been disclosed in prior art for the treatment of infections caused by opportunistic viruses, including for example herpesvirus, with fewer side effects using therapies of natural origin based on the administration of certain amino acids and/or peptides.

Thus, for example, in the article A. R. Gaby, *Natural Remedies for Herpes simplex*, Altern. Med. Rev, 2006, 11 (2), 93-101, some alternative or complementary therapies to aciclovir for the treatment of herpes simplex infections are mentioned, among them the treatment with the amino acid lysine, which exerts an antagonistic mechanism on arginine, which is an amino acid required for the replication of herpes simplex virus.

Also, in the book chapter H. Jensen, *Antimicrobial activity of lactoferrin and lactoferrin derived peptides*, in: *Dietary Protein Research Trends*, J. R. Ling, editor, Nova Science Publishers, New York, 2007, chapter 1, pages 1-62, it is disclosed how the lactoferrin protein present in the milk serum, as well as some specific peptides derived therefrom, have antiviral activity against, among others, the HSV-1 and HSV-2 viruses.

In the German patent application DE-A-3922453 an extract prepared from a hydrolysate of the milk serum proteins is disclosed, which has antiherpetic properties. The proteins from which the hydrolysate is prepared can be alpha-lactalbumin, lactoferrin, beta-lactoglobulin, lysozyme, or serum albumin, all of them present in the milk serum. First, these proteins are hydrolyzed with at least one protease, for example, papain, pancreatin or chymotrypsin, and the residue obtained is extracted with a nonpolar solvent such as petroleum ether, benzene or toluene.

In the international patent application WO-A-92/17191 it is disclosed the use of the dipeptide L-Glu-L-Trp, called Thymogen®, for the treatment, in general, of opportunistic infections in immunocompromised patients, and in particular also for the treatment of herpes.

In the particular case of infections by the human papillomavirus, currently there are few therapeutic resources available for its treatment, although there are some publications in the state of the art in which some agents are proposed having therapeutic activity specifically for HPV infections.

Thus, in the article Mistry et al., *The anti-papillomavirus activity of human and bovine lactoferricin*, Antiviral Res, 2007, 75(3), pp 258-65, a study is disclosed showing the inhibitory activity against HPV-5 and HPV-16 virus infection of some peptides derived from bovine and human lactoferricin protein.

Furthermore, in the international patent application WO-A-00/01720 compositions for treating HPV infections are described, based on the administration of a relatively small peptide that is a peptidomimetic of the E2 protein, a HPV regulatory protein critical for DNA replication and its gene expression, so that these peptidomimetics act by preventing the formation of the complex between E1 and E2 factors, thereby inhibiting viral DNA replication and its proliferation.

Moreover, in the international patent application WO-A-2014/008248 pharmaceutical compositions based on chloroquine, hydroxychloroquine and/or amodiaquine are disclosed, for the treatment of infections associated with human papillomavirus, especially for the treatment of warts of the skin or anogenital warts, by topical or transdermal administration.

In view of the high incidence of infections by opportunistic viruses and the scarce effective therapeutic resources available to combat them, and also the occasionally serious consequences that may result from such infections, there remains a need for new drugs that are effective for the treatment of the pathologies associated with such viruses and that are also effective to prevent the pathological manifestations in infected individuals. Such drugs should be, at the same time effective, practical and safe, so that they involve a minimal risk of side effects.

Object of the Invention

The object of the present invention is the use of a casein hydrolysate as antiviral.

DETAILED DESCRIPTION OF THE INVENTION

The object of the present invention is the use of a casein hydrolysate for the preparation of a medicament for the prevention and/or treatment of infections caused by opportunistic viruses, wherein the hydrolysate comprises peptides wherein the molar fraction of peptides carrying a carboxy terminal proline, expressed in %, is more than two times the molar fraction of proline, expressed in %, in the casein substrate used to generate the hydrolysate; with the proviso that the opportunistic virus is not a herpesvirus.

That is, the object of the invention is a casein hydrolysate for use in the prevention and/or treatment of infections caused by opportunistic viruses, wherein the hydrolysate comprises peptides wherein the molar fraction of peptides carrying a carboxy terminal proline, expressed in %, is more than two times the molar fraction of proline, expressed in %, in the casein substrate used to generate the hydrolysate; with the proviso that the opportunistic virus is not a herpesvirus.

As already disclosed in the international patent application PCT/IB2013/056775 previously filed by the same authors for herpesviruses, the authors of the present invention have surprisingly found that the casein hydrolysate of the invention is extremely effective to achieve rapid remission of the symptoms derived from infections by different opportunistic viruses, and also to prevent or minimize the occurrence of new manifestations of such infections in individuals carrying the virus.

Opportunistic Viruses

Opportunistic viruses are defined as those that although may affect the general population, they are characterized because the occurrence of their infections is particularly high in immunocompromised individuals, in which their symptomatological effects are manifested in a particularly virulent way.

Within the context of the present invention, the following viruses are included under the definition of opportunistic viruses: herpesvirus, human papillomavirus, Molluscum contagiosum virus, hepatitis B virus, hepatitis C virus, JC virus, and BK virus.

In a preferred embodiment of the present invention, the opportunistic virus is human papillomavirus.

Within the context of the present invention, immunocompromised individuals are defined as people whose immune system is weakened, that is, they either have abnormally low levels of the cells involved in the immune system, particularly T lymphocytes and/or B lymphocytes, or do not produce enough antibodies. In this regard, the main causes of immunodeficiency are, for example, infection with the human immunodeficiency virus (HIV), having undergone organ transplantation, or diabetes, among others.

Casein Hydrolysate

The name casein includes a group of phosphoproteins present in the milk, which represents approximately a 3% of the bovine milk. The main components of casein are alpha-, beta-, gamma- and kappa-caseins, among which beta casein is the major fraction of bovine milk.

The casein used as substrate for the hydrolysis is preferably casein from bovine milk, more preferably beta-casein from bovine milk.

The casein hydrolysate used as antiviral according to the use of the present invention, is a hydrolysate whose composition is determined by the use of a proline specific endoprotease in the hydrolysis of the casein, so that the hydrolysate has a composition characterized by a high content of peptides with a proline at the carboxy-terminal end.

In the use of the invention, the molar fraction of the peptides in such hydrolysate carrying a carboxy terminal proline, expressed in %, is more than two times the molar fraction of proline, expressed in %, in the casein substrate used to generate hydrolysate.

The characteristics of this hydrolysate and of the proline specific endopeptidase used in its preparation are described in the international patent application WO-A-02/45524. In that document it is also disclosed the method for determining the molar fraction of the peptides carrying a carboxy terminal proline, expressed in %, as well as the method for determining the molar fraction of proline, expressed in %, in the casein substrate used to generate the hydrolysate.

In this patent application it is disclosed the preparation of protein hydrolysates with a high ratio of proline residues in the carboxyl-terminal position, in the context of the preparation of dietetic protein supplements, especially for sport drinks, with the advantage that such composition has an improved taste, free from the characteristic bitter taste that usually exhibit many of these hydrolysates.

The authors of the present invention have found that, surprisingly, this casein hydrolysate exhibits an excellent therapeutic activity against opportunistic virus infections.

Preferably, the molar fraction of the peptides of this hydrolysate carrying a carboxy terminal proline, expressed in %, is at least three times the molar fraction of proline, expressed in %, in the casein substrate used to generate the hydrolysate.

Preferably, in the casein hydrolysate according to the use of the present invention, the average length of the peptides in the hydrolysate is comprised between 3 and 9 amino acids.

Preferably, the molar fraction of peptides carrying a carboxy terminal proline in the casein hydrolysate is at least 25%, and still more preferably it ranges between 30% and 70%.

Within the context of the present invention, when discussing the molar fraction of peptides, peptides are understood to be those whose molecular mass ranges between 400 and 2000 Dalton, which can be determined, for example, using the liquid chromatography/mass spectrometry (LC/MS) method described in the Materials and Methods section of the international patent application WO-A-02/45524 cited above.

In general, the casein hydrolysate according to the use of the present invention is a hydrolysate where at least the 50% of the casein substrate is hydrolysed. Preferably at least a 10% of the casein substrate is converted into peptides with a molecular mass between 400 and 2000 Dalton, more preferably, between 20% and 90%, and still more preferably between 30% and 80% of the casein substrate is converted into such peptides.

In a preferred embodiment the casein hydrolysate has the following amino acid composition: between 54-64 of lysine, between 22-30 of methionine, between 25-33 of threonine, between 18-26 of histidine, between 26-34 of arginine, between 46-56 of valine, between 34-42 of isoleucine, between 70-80 of leucine, between 33-41 of phenylalanine, between 45-55 of the sum of aspartic acid plus asparagine, between 160-180 of the sum of glutamine plus glutamic acid, between 20-26 of alanine, between 80-90 of proline, between 40-48 of tyrosine, between 37-45 of serine, between 11-17 of glycine, between 0.8-1.2 of cysteine, and between 6-10 of tryptophan; wherein the amounts are expressed in grams of each amino acid per kilogram of hydrolysate.

In a more preferred embodiment the casein hydrolysate has the following amino acid composition: between 57-61 of lysine, between 24-28 of methionine, between 27-31 of threonine, between 20-24 of histidine, between 28-32 of arginine, between 49-53 of valine, between 36-40 of isoleucine, between 73-77 of leucine, between 35-39 of phenylalanine, between 48-52 of the sum of aspartic acid plus asparagine, between 166-176 of the sum of glutamine plus glutamic acid, between 21-25 of alanine, between 82-88 of proline, between 42-46 of tyrosine, between 39-43 of serine, between 13-15 of glycine, between 0.8-1.2 of cysteine and between 7-9 of tryptophan; wherein the amounts are expressed in grams of each amino acid per kilogram of hydrolysate.

In a particularly preferred embodiment the casein hydrolysate has approximately the following amino acid composition: 59 of lysine, 26 of methionine, 29 of threonine, 22 of histidine, 30 of arginine, 51 of valine, 38 of isoleucine, 75 of leucine, 37 of phenylalanine, 50 of the sum of aspartic acid plus asparagine, 171 of the sum of glutamine plus glutamic acid, 23 of alanine, 85 of proline, 44 of tyrosine, 41 of serine, 14 of glycine, 1 of cysteine, and 8 of tryptophan; wherein the amounts are expressed in grams of each amino acid per kilogram of hydrolysate.

A casein hydrolysate according to the specified characteristics is available under the trademark PeptoPro® (DSM). According to its data sheet, this product has applications in food and beverages to enrich their protein content.

Use of the Casein Hydrolysate

The authors of the present invention have noticed that the casein hydrolysate according to the characteristics specified above shows excellent antiviral properties, being effective for the prevention and/or treatment of infections caused by opportunistic viruses.

In an embodiment of the invention, the use relates to the prevention and/or treatment of infections caused by opportunistic viruses selected from the group consisting of human papillomavirus, Molluscum contagiosum virus, hepatitis B virus, hepatitis C virus, JC virus and BK virus.

In a preferred embodiment of the invention, the use relates to the treatment and/or prevention of infections caused by the human papillomavirus.

Within the context of the present invention the term "treatment" refers to the administration of the product with a curative purpose, once some symptoms or external manifestations of the infection have been observed, that will be diverse according to the specific virus, its typology and the nature of the infection. For example, in the case of herpesvirus infections the main clinical manifestations involve pain, burning, inflammation or itching in the affected area, as well as the appearance of pustules, vesicles, blisters, or rash, for example, or other symptoms or specific manifestations. In the case of infection with the human papillomavirus, the main clinical manifestations relate, for example, to the appearance of intraepithelial lesions of the cervix; to papilloma, for example, oral, laryngeal, nasal or conjunctival papilloma; and to warts, whether plantar warts, common warts, flat warts or genital warts (condyloma). In the case of Molluscum contagiosum infection, the symptomatology consists mainly in bumps and skin nodules.

The curative purpose of such treatment is understood as being directed to the elimination, alleviation, improvement, or lessening of the severity of the external manifestations of the infection. Habitually it is not strictly a cure meaning the eradication of the virus, since mainly the opportunistic viruses, as referred to within the context of this invention, may remain in an asymptomatic latent state in the infected individuals throughout their lives, alternating with periods of reactivation. The curative purpose, therefore, is understood as referred to both the removal of the viral infection and the cure of the disease outbreaks of the disease, in order to achieve their remission and the return of the infection to an asymptomatic latent state.

Within the context of the present invention the term "prevention" refers to the administration of the product when there are no symptoms or external manifestations of the infection, but it is administered with a prophylactic purpose with the intention of preventing or delaying the appearance of new outbreaks of the infection, i.e., keeping the infection in an asymptomatic latent state, as well as avoiding susceptible individuals to become infected with the virus, especially immunocompromised individuals.

Within the context of the present invention, the use of casein hydrolysate for the treatment and/or prevention of the stated infections refers to the administration thereof to humans.

In a preferred embodiment, the use according to the present invention relates to the treatment and/or prevention of common warts, plantar warts, flat warts and/or genital warts caused by human papillomavirus.

The aspect of "prevention" is particularly important in human papillomavirus infections, whose clinical manifestations can be benign, but which can lead to serious cancerous diseases, particularly cervical cancer, vaginal cancer, vulvar cancer, anal cancer, penile cancer and oropharyngeal cancer.

Also in the case of hepatitis B virus and hepatitis C virus, prevention is desirable to maintain the infection in an asymptomatic state and thus avoid the disease progression towards development of cirrhosis and liver cancer.

Similarly, in the case of JC virus, prevention is desirable to avoid a serious disease derived from infection by this virus such as progressive multifocal leukoencephalopathy.

In a particularly preferred embodiment, the use according to the present invention relates to the prevention of cervical cancer, vulvar cancer, vaginal cancer, anal cancer, penile cancer and/or oropharyngeal cancer, caused by human papillomavirus.

As the product used in the present invention is completely harmless, derived from the hydrolysis of casein from bovine milk and commonly used as a dietetic supplement, the use according to the present invention has the advantage that it is possible to maintain a long preventive treatment, without the risk of experiencing undesirable side effects, as usually happens with other antiviral treatments, so that the patients taking preventative doses are able to remain without any outbreak of the disease for very long periods, as shown in the examples.

In a preferred embodiment, the use according to the present invention relates to the administration of the casein hydrolysate to immunocompromised individuals. This use is of particular importance within the preventive purpose of the present invention, since it allows preventing the opportunistic virus infections or the clinical manifestation of an already established infection by these viruses in people especially susceptible to develop severe clinical manifestations, such as individuals with impaired immune system.

Thus, in Example 8 it is shown the case of patients infected with human immunodeficiency virus (HIV) which, after being treated with the casein hydrolysate according to the invention, showed no viral infections.

In a preferred embodiment, the use of the casein hydrolysate according to the present invention is characterized in that the hydrolysate is administered orally.

In a more preferred embodiment, the casein hydrolysate is administered according to a daily oral dose comprised between 4 and 40 g. In a still more preferred embodiment, a unit oral dose comprised between 4 and 8 g of the casein hydrolysate is used, and more preferably comprised between 5.5 and 6.5 g, which is administered from 1 to 5 times daily, and more preferably from 1 to 3 times daily.

The casein hydrolysate can also be used preventively before the symptoms appear or after their remission by taking a daily unit oral dose comprised between 4 and 8 g for a period ranging from 12 to 24 months.

In another preferred embodiment, the use of the casein hydrolysate according to the present invention is characterized in that the hydrolysate is administered topically, so that it is locally applied on the area affected by the lesion.

In Examples 3, 4 and 5 some efficacy trials performed with the casein hydrolysate in herpesvirus infections are shown. In those examples the casein hydrolysate was administered to patients suffering from various types of herpes, and in all of them a great efficacy was seen in the relief of symptoms (treatment) as well as in the disappearance or diminution of the reactivation phases (prevention).

Generally within a period of one week, the symptoms of herpes remit completely. In the case of herpes labialis, usually, preferably within 2 to 3 days, and in the case of genital herpes and herpes zoster preferably within 4 to 6 days.

In Examples 6, 7 and 9, some cases are shown in which the casein hydrolysate according to the use of the present invention was effective for the treatment of various lesions associated with human papillomavirus, as well as for preventing clinical symptoms in individuals infected with the virus, achieving its remission to an asymptomatic latent state.

Preparations with the Casein Hydrolysate

The casein hydrolysate according to the use of the present invention typically comes in powder solid form and can be administered either directly or in combination with at least one pharmaceutically acceptable excipient and/or carrier, in the form of a pharmaceutical composition.

It is also part of the object of the present invention, the use of a casein hydrolysate for the preparation of a medicament for the prevention and/or treatment of infections caused by opportunistic viruses, characterized in that the casein hydrolysate is administered in the form of a pharmaceutical composition comprising a pharmacologically effective amount of this hydrolysate and at least one pharmaceutically acceptable excipient and/or carrier, wherein this hydrolysate comprises peptides wherein the molar fraction of peptides carrying a carboxy terminal proline, expressed in %, is more than two times the molar fraction of proline, expressed in %, in the casein substrate used to generate the hydrolysate; with the proviso that the opportunistic virus is not a herpesvirus.

I.e., it is also part of the object of invention a casein hydrolysate for use in the prevention and/or treatment of infections caused by opportunistic viruses, characterized in that the hydrolysate is administered in the form of a pharmaceutical composition comprising this casein hydrolysate and at least one pharmaceutically acceptable excipient and/or carrier, wherein this hydrolysate comprises peptides wherein the molar fraction of peptides carrying a carboxy terminal proline, expressed in %, is more than two times the molar fraction of proline, expressed in %, in the casein substrate used to generate the hydrolysate; with the proviso that the opportunistic virus is not a herpesvirus.

The pharmaceutical composition can be prepared using methods that are well known to the skilled in the art such as those contained in handbooks of pharmaceutical technology, such as the book *Remington The Science and Practice of Pharmacy*, $20^{th}$ edition, Lippincott, Williams & Wilkins, Philadelphia, 2000 [ISBN: 0-683-306472].

The pharmaceutical compositions suitable for the use according to the present invention are all those appropriate for being administered either orally or topically.

In one embodiment of the invention, the pharmaceutical composition is a composition suitable for oral administration. Any pharmaceutical form suitable for oral administration is included within the use according to the object of the present invention, preferably solid compositions in powder or granulate form, or either liquid, in solution, suspension or syrup form, for example.

Preferably, the pharmaceutical composition for oral administration is in powder or granulate form. More preferably, it is in powder form.

In another embodiment of the invention, the pharmaceutical composition is a composition appropriate for topical administration. Any pharmaceutical form suitable for topical administration is included within the use according to the object of the present invention, either in a solid, liquid or semisolid form. Solid compositions for topical administration are generally in powder form, and may include a suitable carrier, such as talc, silica or microcrystalline cellulose, among others. The liquid compositions suitable for topical administration can be prepared by dissolving or dispersing the casein hydrolysate in a suitable carrier such as, for example, water, alcohols, glycols, or mixtures thereof, and are, for example, lotions, liniments, or tinctures; or else this liquid composition can be used to impregnate a support in the form of dressing or bandage that is applied to the affected area; or alternatively the liquid composition can be sprayed onto the affected area using pump sprayers or aerosols. Other forms of topical administration are semisolid compositions such as creams, gels, ointments or pastes.

Preferably, the pharmaceutical composition for topical administration is in the form of a cream, gel, ointment or paste.

The pharmaceutically acceptable excipients that can be used for preparing pharmaceutical compositions in solid form are well known to those skilled in the art and include, for example, diluents such as calcium carbonate, sodium carbonate, magnesium carbonate, magnesium oxide, calcium sulfate, calcium phosphate, sodium chloride, microcrystalline or powdered cellulose, cellulose acetate, ethyl cellulose, dextrates, dextrins, dextrose, lactose, lactitol, fructose, sorbitol, sucrose, maltodextrins, maltose, glyceryl palmitostearate, kaolin, polymethacrylates, pregelatinized starch or starch, among others, and mixtures thereof; lubricants, such as calcium stearate, magnesium stearate, talc, stearic acid, glyceryl behenate, glyceryl palmitostearate, sodium benzoate, sodium lauryl sulfate, sodium stearyl fumarate, or hydrogenated castor oil, among others, and mixtures thereof; disintegrants such as alginic acid, sodium croscarmellose, crospovidone, sodium starch glycolate, starch, low-substituted hydroxypropylcellulose, among others, and mixtures thereof; binding agents such as sodium carboxymethylcellulose, cellulose acetate phthalate, dextrates, dextrin, ethylcellulose, guar gum, maltodextrin, methylcellulose, microcrystalline cellulose, povidone, pregelatinized starch, stearic acid, or sucrose, among others, and mixtures thereof; anticaking agents such as tribasic calcium phosphate, calcium silicate, colloidal silica, magnesium silicate, magnesium trisilicate, or talc, among others, and mixtures thereof; thickening agents such as colloidal silica, dextrin, ethylcellulose, hydroxyethyl cellulose, hydroxyethylmethyl cellulose, hypromellose, polyethylene glycol, trehalose, xanthan gum, among others, and mixtures thereof; suspending agents such as xanthan gum, guar gum, alginic acid, bentonite, carbomers, sodium or calcium carboxymethylcellulose, hydroxyethyl cellulose, hydroxypropyl cellulose, hydroxypropylmethyl cellulose, hydroxypropyl alginate, microcrystalline or powdered cellulose, anhydrous colloidal silica, dextrins, gelatins, kaolin, magnesium aluminum silicate, maltitol, povidone, sorbitan esters, or tragacanth, among others, and mixtures thereof; stabilizing agents such as guar gum, xanthan gum, alginic acid, ascorbic acid, calcium stearate, sodium carboxymethylcellulose, calcium carboxymethylcellulose, ethylcellulose, lecithin, monoethanolamine, potassium chloride, povidone, sorbitol, or xylitol, among others, and mixtures thereof; flavoring agents such as maltol, vanillin, ethyl vanillin, menthol, citric acid, fumaric acid, ethyl maltol, tartaric acid, peppermint, artificial or natural fruit aromas, among others, and mixtures thereof; sweetening agents such as sorbitol, maltitol, mannitol, dextrose, maltose, xylitol, saccharin, sucrose, sucralose, aspartame, acesulfame potassium, or trehalose, among others, and mixtures thereof; coloring agents such as curcumin, lactoflavin, iron oxides (red, yellow or black), caramel, lactoflavin phosphate, cochineal red, titanium dioxide, or carotenes, among others, and mixtures thereof; or mixtures thereof.

Some of the excipients and carriers suitable to be used in the liquid formulations, in the form of solutions, or suspensions are, for example, solvents such as water, alcohol, almond oil, castor oil, glycerin, among others; buffering agents such as diethanolamine, dibasic sodium phosphate, monobasic sodium phosphate, potassium citrate, sodium bicarbonate, sodium citrate dihydrate, among others, and mixtures thereof; viscosity modifiers such as alginic acid, bentonite, carbomers, carrageenan, gelatin, glycerin, hydroxyethyl cellulose, hydroxyethylmethyl cellulose, hydroxypropyl cellulose, maltodextrin, polyvinyl alcohol, sodium alginate, tragacanth, arabic gum, or xanthan gum, among others and mixtures thereof; emulsifying agents such as calcium stearate, cetyl alcohol, ethylene glycol palmitostearate, glyceryl monostearate, lecithin, oleic acid, poloxamers, sodium lauryl sulfate, sorbitan esters, polyoxyethylene castor oil derivatives, or emulsifying wax, among others, and mixtures thereof; suspending agents such as xanthan gum, guar gum, alginic acid, bentonite, carbomers, sodium or calcium carboxymethylcellulose, hydroxyethyl cellulose, hydroxypropyl cellulose, hydroxypropylmethyl cellulose, hydroxypropyl alginate, microcrystalline or powdered cellulose, anhydrous colloidal silica, dextrins, gelatins, kaolin, magnesium aluminum silicate, maltitol, povidone, sorbitan esters, or tragacanth, among others, and mixtures thereof; flocculating agents such as sodium acetate, sodium phosphate, sodium citrate, sodium lauryl sulfate, starch, alginates, tragacanth, or carbomers, among others, and mixtures thereof; wetting agents as benzalkonium chloride, sodium docusate, sodium lauryl sulfate, sorbitan esters, polyoxyethylene stearates or polyoxyethylene sorbitan fatty acid esters, among others, and mixtures thereof; preservatives such as benzalkonium chloride, benzyl alcohol, bronopol, parabens, sodium benzoate, sodium propionate, sorbic acid or thimerosal, among others, and mixtures thereof; flavoring agents as maltol, vanillin, ethyl vanillin, menthol, citric acid, fumaric acid, ethyl maltol, tartaric acid, peppermint, artificial or natural fruit aromas, among others, and mixtures thereof; sweetening agents such as sorbitol, maltitol, mannitol, dextrose, maltose, xylitol, saccharin, sucrose, sucralose, aspartame, acesulfame potassium or trehalose, among others, and mixtures thereof; coloring agents such as curcumin, lactoflavin, iron oxides (red, yellow or black), caramel, lactoflavin phosphate, cochineal red, titanium dioxide, or carotenes, among others, and mixtures thereof; or mixtures thereof.

The semisolid topical formulations in the form of creams, gels, ointments or pastes comprise a pharmaceutically acceptable carrier in which the casein hydrolysate is dissolved, emulsified, dispersed or suspended. This carrier is selected from water, a non-aqueous water miscible carrier, such as for example ethanol or isopropanol, and a non-aqueous water-immiscible carrier, such as for example paraffin oil. Optionally, such semisolid compositions for topical administration contain a pharmaceutically acceptable excipient such as, for example, surfactant and emulsifier agents, lipidic and emollient compounds, consistency factors and thickening agents, stabilizers, hydrotropes, preservative agents, essences, coloring agents, silicone compounds, fats, waxes, lecithins, phospholipids, UV sun protection factors, or mixtures thereof.

The excipients suitable to be used in the pharmaceutical compositions of the present invention are well known to those skilled in pharmaceutical technology and are described, for example, in the book R. C. Rowe, P. J. Sheskey and P. J. Weller, *Handbook of Pharmaceutical Excipients*, Fourth Edition, Pharmaceutical Press, 2003.

In a preferred embodiment, the pharmaceutical composition is in the form of powder or granulate for oral use. The powder is usually prepared by mixing the casein hydrolysate in powder form with at least one pharmaceutically acceptable excipient. The granulate consists of powder particles that have been aggregated to form larger particles, and it is prepared according to procedures which are well known to those skilled in the art, such as dry granulation or wet granulation.

The compositions in the form of powder or granulate are usually taken after dissolution or dispersion in water or another liquid.

In one embodiment of the invention, the powder or granulate composition is presented in a bulk container as, for example, in a glass container with a wide opening, so that the required dose for each administration is taken as needed, preferably with the help of a measurement device or dispenser to measure the dose to be administered.

In another embodiment of the invention, the powder or granulate composition is presented in the form of monodose sachets, containing the unit dose suitable for oral administration. Those sachets can be made of paper or either of aluminum or plastic laminates. Preferably, the oral unit dose comprises between 4 and 8 g of the casein hydrolysate, more preferably between 5 and 7 g, and still more preferably about 6 g of the hydrolysate.

In a particularly preferred embodiment of the invention, the composition for oral use is in powder form. More preferably, the composition in powder form comprises the casein hydrolysate, and a pharmaceutically acceptable excipient which is selected from sweeteners, flavoring agents and coloring agents, or mixtures thereof.

Preferably, the composition in powder form contains a quantity of the casein hydrolysate comprised between 70% and 99%, and more preferably comprised between 80% and 95%, expressed as weight ratio relative to the total weight of the composition.

In another preferred embodiment of the invention, the pharmaceutical composition according to the use of the present invention is a composition for topical administration, preferably in the form of cream, gel, ointment or paste. Preferably, this composition for topical administration comprises an amount of the casein hydrolysate comprised between 5% and 25%, and more preferably comprised between 7% and 15%.

Creams, as it is well known to those skilled in pharmaceutical technology are semisolid emulsions, which can be of the oil-in-water (o/w) type or water-in-oil (w/o) type, formulated from an oil phase, an aqueous phase and an emulsifying agent. The oil phase consists of a carrier which can be, for example, liquid paraffin or a vegetable oil such as, for example, castor oil, almond oil, peanut oil, sesame oil, cottonseed oil or corn oil.

Gels are obtained from a liquid that is gelled by adding a rheological agent or a gelling agent. Some of the gelling agents suitable to be used in the present invention are, for example, carrageenan, guar gum, tragacanth gum, locust bean gum, pectin, agar, alginic acid, carbomers, carboxymethylcellulose, methylcellulose, hydroxyethyl cellulose, hydroxypropylmethyl cellulose, and polyethylene glycol, among others.

Ointments are semisolid fat preparations, which contain the active ingredient dissolved or in dispersed form. Ointments can be formulated with various vehicles such as paraffin, plastibases (a mixture of polyethylene with a series of hydrocarbons), vegetable oils, such as peanut oil, sesame oil, olive oil, cottonseed oil, almond oil, corn oil, silicones or polyethylene glycols, among others, or with a mixture thereof.

Pastes are prepared analogously to the ointments, and they show a more solid consistency since they contain greater amounts of insoluble solids.

Next, some examples are provided with the purpose of illustrating the invention, but not limiting it.

EXAMPLES

Example 1

Preparation of a Composition in Powder Form

A composition in powder form was prepared using the following components:

| Ingredient | Weight (g/unit dose) | % (weight) |
|---|---|---|
| Casein hydrolysate | 6 | 91.58 |
| Sucralose | 0.050 | 0.76 |
| Lemon flavor | 0.50 | 7.63 |
| Coloring agent | 0.002 | 0.03 |

All ingredients were thoroughly mixed until obtaining a homogeneous mixture and the mixture was introduced into a monodose sachet.

Each monodose sachet contained 6 g of casein hydrolysate.

Example 2

Preparation of a Composition in Cream/Lip Balsam Form

A composition in a cream form was prepared using the following components:

| Ingredient | % (weight) |
|---|---|
| Casein hydrolysate | 10.00 |
| Aroma | 1.00 |
| Emulsifier | 5.00 |
| Waxes | 15 |
| Water | q.s. |

The composition was prepared following procedures that are well known to the skilled in the art.

Example 3

Efficacy Study in Herpes Labialis

The efficacy of the orally administered casein hydrolysate was tested for the treatment and prevention of herpes labialis.

12 patients suffering from herpes labialis (7 men and 5 women) were treated, their ages comprised between 17 and 56 years. This patient group periodically presented outbreaks of the disease, with a frequency ranging from 3 to 12 per year, with an average of 7.2 outbreaks per year for this group. During the treatment, 2 monodose sachets of the powder product prepared in Example 1 were administered daily, containing 6 g of the protein hydrolysate in each sachet.

In all the cases, the product was effective for the treatment of herpes labialis, so that after 2 to 3 days of treatment, the complete remission of the symptoms was achieved for all the patients.

Once the symptoms had disappeared, 8 of these patients continued to take one monodose sachet of the product daily, as a maintenance dosage regimen to prevent the appearance of further outbreaks of the infection, for a period of time comprised between 13 and 24 months, depending on the case. In all cases it was managed to avoid the appearance of new outbreaks of herpes labialis, during the maintenance dosage regimen.

Example 4

Efficacy Study in Genital Herpes

In this example, the efficacy of the orally administered casein hydrolysate was tested for the treatment and prevention of genital herpes.

6 patients suffering from genital herpes (3 men and 3 women) were treated, their ages comprised between 19 and 42 years. During the treatment, 3 sachets of the powder product prepared in Example 1 were administered daily, containing 6 g of the protein hydrolysate in each sachet. In all cases, the complete cure of the symptoms of genital herpes was achieved after from 4 to 6 days of treatment.

After the remission of the symptoms, the patients continued taking 1 monodose sachet of the product daily for 12 and 18 months and with this dosage no new outbreaks of the disease were observed. Therefore, the product was also effective for the prevention of new episodes of genital herpes.

Example 5

Efficacy Study in Herpes Zoster

The efficacy of the orally administrated casein hydrolysate was tested for the treatment and prevention of herpes zoster. In this study the monodose sachets of the powder product prepared in Example 1 were also employed.

5 patients suffering from herpes zoster (2 men and 3 women) were treated, their ages comprised between 39 and 80 years, and presenting affectation in the back, or in the abdomen, or in the legs and the abdomen.

The administration of 4 sachets of the product daily allowed the healing of the symptoms after 4 or 5 days of treatment, for all the patients of the study.

The patients continued for between 12 and 18 months in a preventive dosage regimen, with one sachet of the product daily, thereby a decrease in the number of recurrences of herpes zoster was observed, as well as a decrease in their virulence, for all patients of the study.

Example 6

Preventative Efficacy Study in Human Papillomavirus Infected Patients

The efficacy of the orally administered casein hydrolysate was tested for the prevention of the appearance of clinical symptoms in two patients diagnosed as carriers of human papillomavirus (HPV), a 38-year-old woman and a 35-year-old man.

In both cases, from the detection of the infection, they were subjected to a preventive protocol, in which they were given one daily sachet of the powder product prepared in Example 1 containing 6 g of casein hydrolysate in each sachet. After four weeks of such treatment, no clinical signs were detected, and in particular the woman had not developed any evolution of cervical dysplasia, and neither any symptoms of viral evolution outbreak were observed in the male.

Example 7

Therapeutic and Preventive Efficacy Study in Genital Lesions by Human Papillomavirus The efficacy of the oral casein hydrolysate was tested in the treatment and prevention of condyloma (genital warts) caused by HPV.

4 male patients aged 25 to 35 years with active outbreaks of HPV presenting condylomas were treated with one monodose sachet daily containing 6 g of protein hydrolysate, according to the preparation described in Example 1, for 15 days and after this period, condylomas had reverted in all cases.

The four patients continued taking the product on a prophylactic regimen, according to a dosage of one sachet per week. After two months in preventive treatment, no reappearance of the lesions was observed in any of the cases.

Example 8

Efficacy Study in the Prevention of Opportunistic Virus Infections in HIV Positive Patients 5 patients diagnosed HIV positive in different stages of evolution, after the ingestion of one sachet daily for 4 months showed absence of viral infections according to the analytical results and clinical observation.

Example 9

Therapeutic Efficacy Study Against Mouth Lesions by Human Papillomavirus

A HIV-positive male patient aged 33 having mouth ulcers due to human papillomavirus was treated with one daily sachet of the casein hydrolysate prepared in Example 1 for 3 months, after which a complete remission of the lesions was observed, while a visible improvement was already noticeable after the first 15 days.

The invention claimed is:
1. A method for the treatment of human papilloma virus infections, comprising administering to a patient in need thereof, an effective amount of a casein hydrolysate, the hydrolysate comprising peptides wherein the molar fraction of peptides carrying a carboxy terminal proline, expressed in %, is more than two times the molar fraction of proline, expressed in %, in the casein substrate used to generate the hydrolysate.

2. The method according to claim 1, wherein the molar fraction of the peptides in the hydrolysate carrying a carboxy terminal proline, expressed in %, is at least three times the molar fraction of proline, expressed in %, in the casein substrate used to generate the hydrolysate.

3. The method according to claim 1, wherein the average length of the peptides in the casein hydrolysate is between 3 and 9 amino acids.

4. The method according to claim 1, wherein the molar fraction of peptides carrying a carboxy terminal proline in the casein hydrolysate is at least 25%.

5. The method according to claim 1, wherein the molar fraction of peptides carrying a carboxy terminal proline in the casein hydrolysate is between 30% and 70%.

6. The method according to claim 1, wherein the casein hydrolysate comprises an amino acid composition of between 54-64 of lysine, between 22-30 of methionine, between 25-33 of threonine, between 18-26 of histidine, between 26-34 of arginine, between 46-56 of valine, between 34-42 of isoleucine, between 70-80 of leucine, between 33-41 of phenylalanine, between 45-55 of the sum of aspartic acid plus asparagine, between 160-180 of the sum of glutamine plus glutamic acid, between 20-26 of alanine, between 80-90 of proline, between 40-48 of tyrosine, between 37-45 of serine, between 11-17 of glycine, between 0.8-1.2 of cysteine, and between 6-10 of tryptophan; wherein the amounts are expressed in grams of each amino acid or the sum of amino acids per kilogram of hydrolysate.

7. The method according to claim 1, wherein administration treats and/or prevents one or more of common warts, plantar warts, flat warts and/or genital warts.

8. The method according to claim 1, wherein the casein hydrolysate is administered to immunocompromised individuals.

9. The method according to claim 1, wherein the casein hydrolysate is administered orally.

10. The method according to claim 9, wherein the casein hydrolysate is administered according to a daily dose comprised between 4 and 40 g.

11. The method according to claim 9, wherein a unit oral dose of between 4 and 8 g of the casein hydrolysate is used, wherein the unit oral dose is administered from to 5 times daily.

12. The method according to claim 1, wherein the casein hydrolysate is administered topically.

13. The method according to claim 1, wherein the casein hydrolysate is administered in the form of a pharmaceutical composition comprising a pharmacologically effective amount of the hydrolysate and at least one pharmaceutically acceptable excipient and/or carrier.

14. The method according to claim 13, wherein the pharmaceutical composition is a composition suitable for oral administration.

15. The method according to claim 14, wherein the pharmaceutical composition is in powder or granulate form.

16. The method according to claim 15, wherein the composition is dosed in monodose sachets containing between 4 and 8 g of the casein hydrolysate.

17. The method according to claim 13, wherein the pharmaceutical composition is a composition suitable for topical administration.

18. The method according to claim 17, wherein the pharmaceutical composition is in the form of cream, gel, ointment or paste.

19. The method according to claim 1, wherein administration treats and/or prevents genital warts.

* * * * *